United States Patent
Garcia, Jr.

(10) Patent No.: US 7,125,398 B2
(45) Date of Patent: Oct. 24, 2006

(54) MEDICAL NEEDLE GUARD

(76) Inventor: Raul Garcia, Jr., 10813 Loma Del Norte, El Paso, TX (US) 79934

( * ) Notice: Subject to any disclaimer, the term of this patent is extended or adjusted under 35 U.S.C. 154(b) by 624 days.

(21) Appl. No.: 10/427,202

(22) Filed: Apr. 30, 2003

(65) Prior Publication Data

US 2004/0220528 A1  Nov. 4, 2004

(51) Int. Cl.
*A61M 5/00* (2006.01)
*A61M 5/32* (2006.01)

(52) U.S. Cl. .................................. 604/263; 604/192
(58) Field of Classification Search ............... 604/263, 604/192, 198, 110, 165.03
See application file for complete search history.

(56) References Cited

U.S. PATENT DOCUMENTS

| | | | |
|---|---|---|---|
| 4,627,843 A * | 12/1986 | Raines | 604/263 |
| 4,735,618 A | 4/1988 | Hagen | |
| 5,531,704 A | 7/1996 | Knotek | |
| 5,951,522 A | 9/1999 | Rosato et al. | |
| 5,951,525 A * | 9/1999 | Thorne et al. | 604/198 |
| 5,997,504 A | 12/1999 | Bell | |
| 6,261,259 B1 | 7/2001 | Bell | |
| 6,537,255 B1 | 3/2003 | Raines | |
| 6,719,731 B1 * | 4/2004 | Parmigiani | 604/192 |
| 6,824,530 B1 * | 11/2004 | Wagner et al. | 604/162 |
| 6,949,086 B1 * | 9/2005 | Ferguson et al. | 604/198 |
| 2001/0039401 A1 * | 11/2001 | Ferguson et al. | 604/198 |
| 2002/0072716 A1 | 6/2002 | Barrus et al. | |
| 2002/0099338 A1 | 7/2002 | Young | |
| 2002/0169425 A1 | 11/2002 | Guzzo et al. | |
| 2003/0229317 A1 * | 12/2003 | Ferguson et al. | 604/263 |

* cited by examiner

*Primary Examiner*—Sharon Kennedy
(74) *Attorney, Agent, or Firm*—Faier & Faier P.C.; Martin Faier; James M. Faier

(57) ABSTRACT

The present invention provides a needle guard comprising a base having a needle well to guide the point of a needle into the patient and, at the same time, for confining the pointed end of a needle within the walls of the needle well until the needle is inserted into a patient. The base is connected by at least a connector to a handle. The connector is constructed to allow the needle to be pushed beyond the needle well thereby exposing the needle. The connector also limits the extent to which the needle can be retracted. This prevents the needle from being pulled past the needle well as the needle is extracted from the patient. As a consequence of the construction, the point of the needle is substantially maintained within the needle well, except when the needle is inserted into the patient. The present invention also provides a method and an assembly for safely handling a medical needle by keeping the needle point confined within the needle well prior to insertion into a patient, and after retraction from the patient.

16 Claims, 4 Drawing Sheets

MEDICAL NEEDLE GUARD

FIELD OF THE INVENTION

The present invention provides a needle guard for handling a medical needle, an assembly of the needle guard and the medical needle, and a method of using the needle guard to safely insert and/or retract the medical needle from a patient, and in the case of infusion needles into and out of the access port of a vascular access device within the patient.

BACKGROUND

In the modern age of AIDS, hepatitis and other blood-borne diseases, needle-stick injuries pose a grave concern to the medical field. It is therefore not surprising that various safety devices have been proposed to make the use of medical needles in general, and infusion needles in particular, safer for the clinician to use. Some examples of such devices are found in U.S. Pat. No. 6,537,255 to Raines, U.S. 2002/0169425 to Guzzo et al., U.S. 2002/0072716 to Barrus et al., U.S. Pat. No. 6,261,259 to Bell, U.S. Pat. No. 5,951,522 to Rosato et al., U.S. Pat. No. 5,584,813 to Livingston et al. and U.S. Pat. No. 4,631,058 to Raines. In addition, a hinged-wall system has been proposed in U.S. Pat. No. 5,531,704 to Knotek. Nevertheless, because the consequence of needle-stick injuries can be particularly severe, there is an ongoing demand to optimize the safety of handling needles.

When a patient requires constant or prolonged administration of a fluid or a drug dissolved in a fluid medium, it is known to implant a vascular access device to provide a convenient method of administration. Such devices are also used to remove fluids from the patient. Typically, the vascular access device is implanted subcutaneously adjacent to an area to be treated, such as the chest or the abdomen.

Vascular access devices usually comprise an access port or septum positioned under the skin. To administer or remove fluids, an infusion needle called the Huber needle is often used. The Huber needle often has an approximately 90 degree bend which separates the needle into a first section with a sharpened or pointed end, and a second section with an end for connecting to medical tubing that is capable of being connected to a source of fluids. The end of the second section may or may not be specially adapted with connectors to make connection to a medical tube easier. When used, the pointed end is pressed down in a substantially perpendicular direction relative to the surface of the skin over the access port. Once inserted, the second section is substantially parallel to the skin surface, and can be secured, by for example, tape to the patient.

It is well-known that Huber needles are particularly difficult to insert and/or remove from the access ports. This presents a particularly dangerous hazard to clinicians, because a force sufficient to insert or remove the needle may also cause an accidental needle-stick injury to the clinician. Moreover, when such needles are used with a vascular access device, they also have a "rebound" or "bounce back" effect, wherein to counter a sufficient force to remove such needles, a corresponding opposing force is exerted which causes the needle to rebound or bounce back towards the origin of the force. This rebound effect increases the likelihood of an accidental needle-stick, when the clinician attempts to remove the needle from the access port.

Moreover, medical needles, such as hypodermic needles, phlebotomy needles, intravenous needles, etc., have also been implicated in substantial number of accidental needle-stick injuries. It would be useful to have a device which will confine the point of the needle within a relatively tight space until the needle is inserted into a patient, and will permit the needle to be inserted with minimal or no exposure outside of the tight space, or the patient. It is presumed that one of ordinary art would understand that, for the most part, the needles referred to herein are hollowed medical needles with an opening on each end to allow passage of fluid therethrough.

SUMMARY OF THE INVENTION

The present invention provides a needle guard comprising a base having a needle well to guide the point of a needle into the patient and, at the same time, for confining the pointed end of a needle within the walls of the needle well until the needle is inserted into a patient. The base is connected by at least a connector to a handle. The connector is constructed to allow the needle to be pushed beyond the needle well thereby exposing the needle. The connector also limits the extent to which the needle can be retracted. This prevents the needle from being pulled past the needle well as the needle is extracted from the patient. As a consequence of the construction, the point of the needle is substantially maintained within the needle well, except when the needle is inserted into the patient. The present invention also provides a method and an assembly for safely handling a medical needle by keeping the needle point confined within the needle well prior to insertion into a patient, and after retraction from the patient.

DETAILED DESCRIPTION

The invention is described by the following examples. It should be recognized that variations based on the inventive features disclosed herein are within the skill of the ordinary artisan, and that the scope of the invention should not be limited by the examples. To properly determine the scope of the invention, an interested party should consider the claims herein, and any equivalent thereof. In addition, all citations herein are incorporated by reference.

Figure 1:
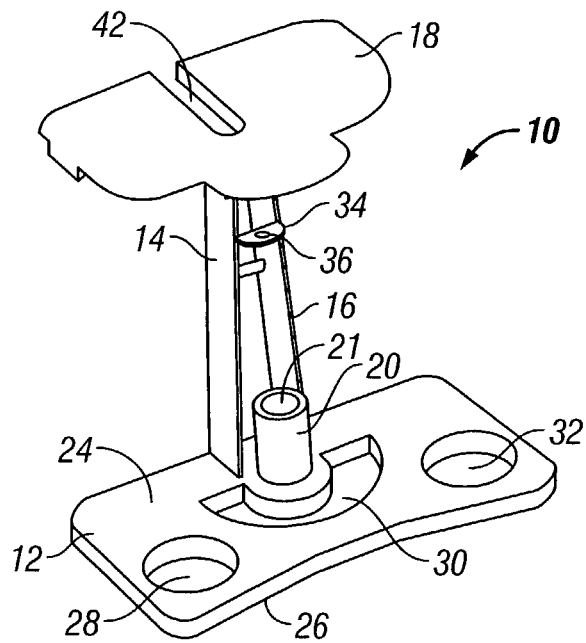
FIG. 1 is a perspective front view of a needle guard.

In FIG. 1, an embodiment of a needle guard 10 according to the invention is shown. The needle guard comprises a base 12 attached by a first connector 14 and a second connector 16 to a handle 18. Base 12 further comprises a base top 24 having a guide 20 that surrounds a space above base top 24. Guide aperture 21 extends through guide 20, and provides a passage for the needle to extend through guide 20. Although a guide 20 is not needed, when it is present, guide aperture 21 constitutes part of the needle well 22 to guide the needle point. In that case, the walls of the needle well 22 would necessarily include the walls of guide 20.

The needle well 22 extends through base 12, from base top 24 to base bottom 26. If there is a guide 20, needle well 22 also includes any guide aperture 21 of the guide 20. Base 12 may also comprise optional positioning gaps, such as those shown as positioning gaps 28, 30 and 32. In the illustrated embodiment, positioning gap 30 is located adjacent to guide 20 and well 22 to provide a means to locate the appropriate insertion area of the patient.

A needle holder 34 is attached to both first connector 14 and second connector 16. The needle holder 34 is located closer to handle 18 than base 12, and comprise a bore 36 which is formed to intimately secure a needle. In another embodiment, needle holder 34 is integral to the underside of handle 18. In a further embodiment, bore 36 has some play so that needle holder 34 can slide up and down the needle, as the needle is inserted and retracted. Other methods of securing the needle to the needle guard may include adhesive bonding agents, UV-cured adhesives, clips, runners, and such.

Figure 2:
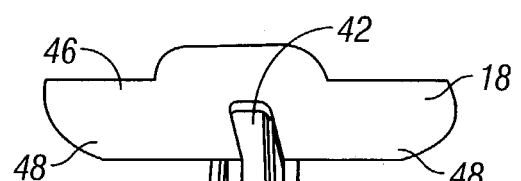
FIG. 2 is a perspective rear view of a needle guard.

In FIG. 2, connectors 14 and 16 are shown with an optional integral lock with lock parts 38 and 40 to lock needle guard 10 in a secured position when the needle is not being used. Though shown as opposing latches, different locking mechanisms are known in the field. For example, lock parts 38 and 40 can be complementary male and female tabs, or a head and recess locking means. Moreover, the function of lock parts 38 and 40 need not be performed by an integral part. Connector 14 and 16 may also be secured by a clip or a locking pin that is inserted into locking holes in the connectors (not shown). Needle guard 10 may also be secured by a stopper that physically separates the base from the handle. In an embodiment, the locking mechanism is used after the needle is retracted from the patient. In another embodiment, the locking mechanism is used before the needle is inserted, can be unlocked when the needle is to be inserted, and then locked when the needle is retracted.

Figure 3:
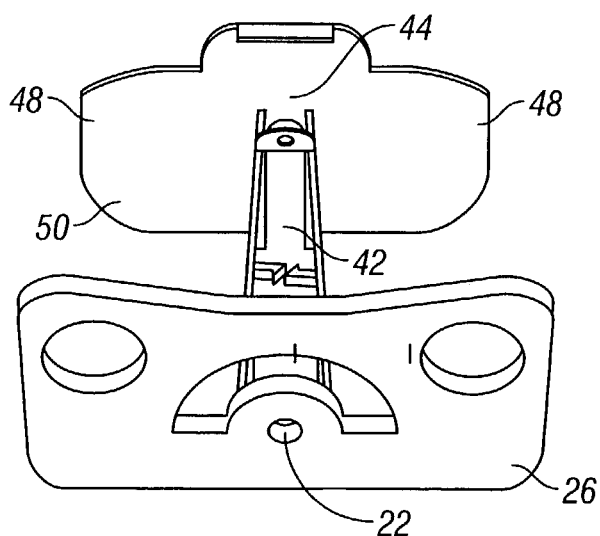
FIG. 3 is a perspective front and bottom view of a needle guard.

Handle 18 is shown as a substantially horizontally flat structure with an optional groove 42 formed to provide sufficient clearance to insert a medical needle. In the embodiment shown in FIG. 3, handle 18 has a lip 44 adjacent groove 42 to provide additional pressure against a partially horizontal part or connector to a medical needle when inserting the needle into the patient. In the present embodiment, handle top 46 provides a surface for a clinician to press down when inserting the needle. Handle wings 48 provide a handle for the clinician pulls the wings by handle bottom 50 to extract the needle from the patient.

Figure 4:
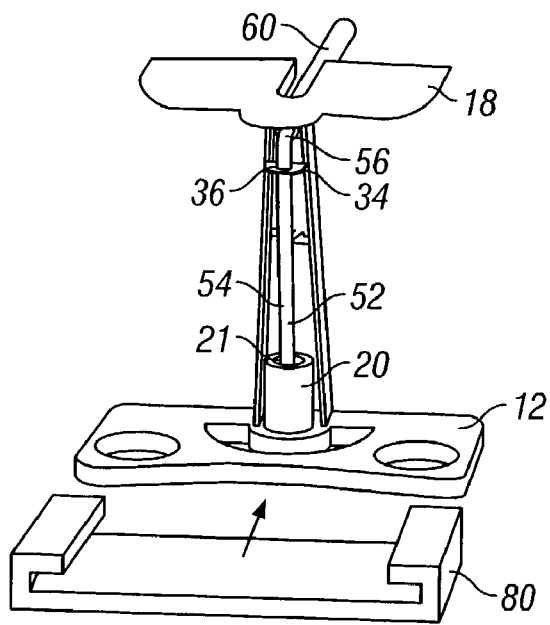
FIG. 4 is a perspective front view of a needle guard assembly with an optional separate needle cover.
Figure 5:
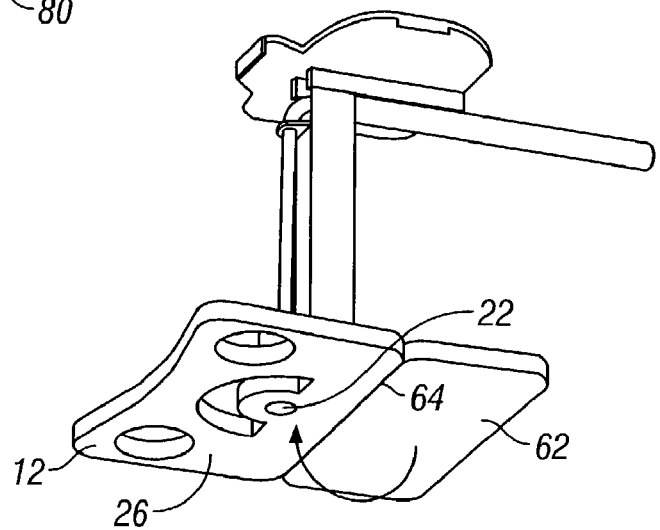
FIG. 5 is a perspective bottom and side view of a needle guard assembly with an optional integral needle cover.
Figure 6:
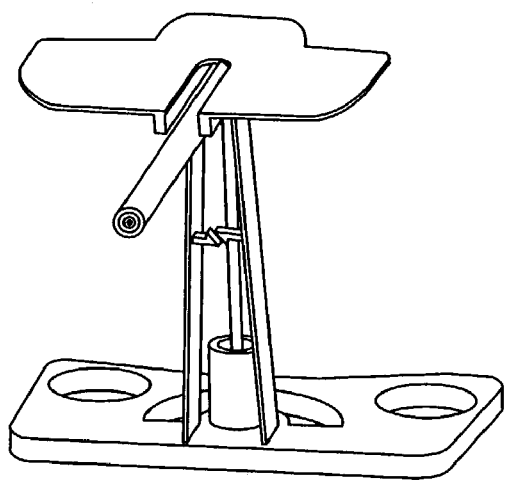
FIG. 6 is a perspective rear view of a needle guard assembly.
Figure 7:
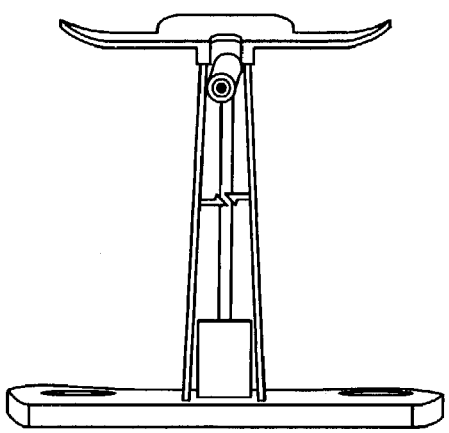
FIG. 7 is a rear view of a needle guard assembly.

In FIG. 4, a needle 52 with two sections is assembled with needle guard 10 to form a guarded needle assembly. As illustrated here, needle 52 has a piercing section 54 which is separated from a connector section 56 by a substantially right angle. The particular severity of the angle is not crucial to the invention. As shown, the piercing section 54 of needle 52 is inserted through bore 36 of needle holder 34, then into guide 20 such that the pointed end 58 (see FIGS. 8 and 9) of the needle is secured within the walls of needle well 22. In the present embodiment, medical tubing 60 is attached to and substantially envelopes connector section 56. An optional separate sliding cover is also shown which is capable of slipping over base 12 along base bottom 26 and has holders that secures the cover along the edges of base 12 to keep the needle well 22 covered when the needle is not in use. In FIG. 5, the needle assembly is shown with an optional integral needle cover 62, which is attached to base 12 by a scored section 64 which acts as a hinge. Needle cover 62 can be swung in the direction of the arrow shown to cover all or a portion of base bottom 26 so that needle well 22 is covered when the needle is not in the patient. In another embodiment, needle cover 62 and base 12 have an integral locking mechanism, whereby needle cover 62 can be locked in-place to base 12. Different locking mechanisms are known in the field, and can include, for example, male and female tabs, and head and recess locking means.

Figure 8:
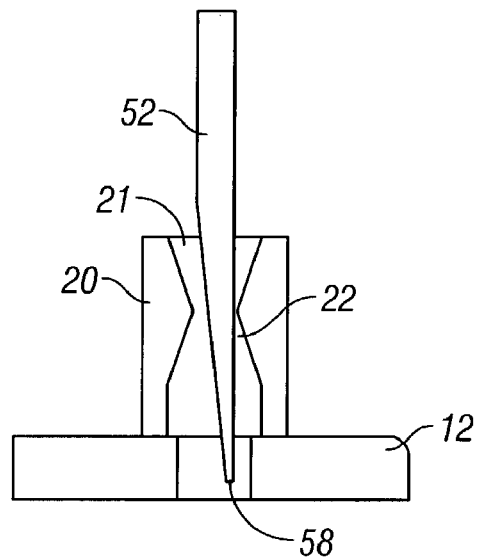
FIG. 8 is a cross-sectional side view of a needle guard assembly showing the point of the needle surrounded by the needle well.

In FIG. 8, a side cross-section is shown of needle 52 within needle well 22. Although shown with pointed end 58 in needle well 22, the pointed end can reside anywhere within needle well 22, including within guide aperture 21, to be secured. This is the position of the needle prior to use, or after it is secured in the inactive position, upon withdraw from the patient.

Figure 9:
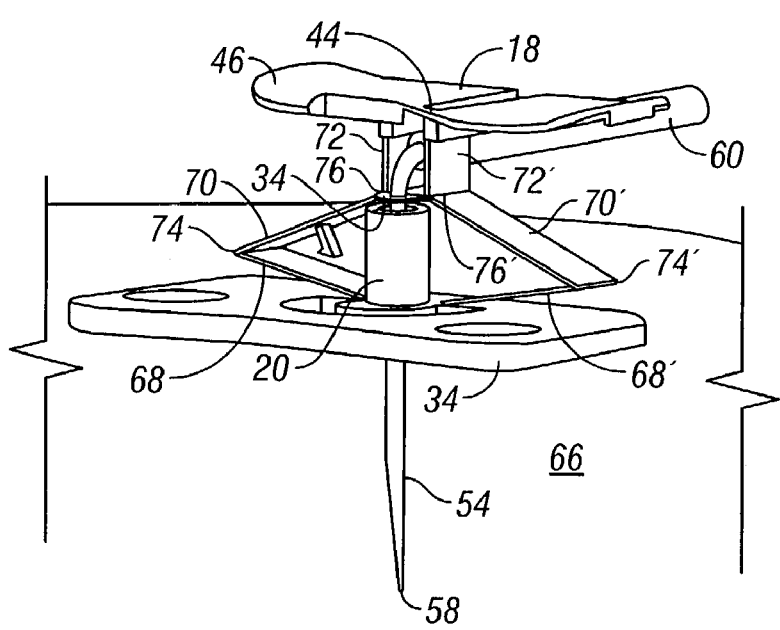
FIG. 9 is a perspective front view of a needle guard assembly in its activated state, where the needle is pushed beyond the needle well.
Figure 10:
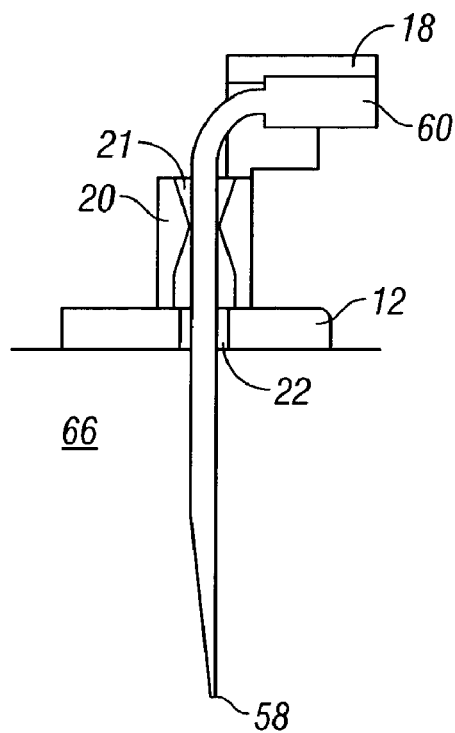
FIG. 10 is a cross-sectional side view of a needle guard assembly showing the point of the needle pushed beyond the needle well.

When used, the clinician uses base 12 and optionally locating gaps 28–32 to place the assembly on the patient, so that the needle is above the port of the vascular access device. Once the proper location is found, the clinician can press against base top 24 to secure the base 12 of the assembly against the patient. The clinician can with the same hand, or a different hand, press down against handle top 46 to insert the needle into the patient. Obviously, if needle well 22 is covered, one needs to uncover the well before attempting to insert the needle. The activated needle is shown in FIGS. 9 and 10 with a portion of piercing section 54 inserted into the patient. The vascular access device is not shown, because the assembly need not be used with the vascular access device. The needle guard can be used any time a medical needle is indicated for the patient. Note that in the present embodiment, connectors 14 and 16 are shown as accordion walls having three walls (68, 70, 72 for one connector, and 68', 70', 72' for the other connector) each having a hinge that allows the accordion to fold out (74 and 74'), and a hinge that allows the accordion to fold downwards (76 and 76'). Other embodiments of the connectors, may include, telescoping walls, springs or a material that can be resiliently compressed (not shown). In alternative embodiments, a single connector that surrounds the needle well may be used.

When activated, and the clinician presses down against handle top 46 so that connectors 14 and 16 folds out to provide room for the needle to plunge down (FIG. 9). In one embodiment, the downward force is transmitted through the needle holder 34 because bore 36 substantially secures the needle to the connectors. In another embodiment, bore 36 has sufficient play, such that needle holder 34 can slide along needle 52 until lip 44 presses against an at least partially horizontal section of the needle, or a connector to the needle. In the embodiment shown here, lip 44 can press down on connector section 56 or tubing 60 at the end proximate to piercing section 54, to transmit the downward force against the needle. In this case, the force is directed downward substantially along the linear axis of the piercing section 54 of needle 52, to provide an optimal penetrating force that is perpendicular to the surface of the patient. In addition, guide 20 prevents the needle from sliding along the surface of the patient and causing unintended needle stick injuries. FIG. 10 provides a sectional view of the assembly when the needle is inserted into patient 66. Once in the patient, the entire assembly can be taped to the patient.

To remove the needle from the patient, a clinician can secure the bottom of the assembly by pressing down on base top 24. Then the clinician can pull handle 18 up by applying force against handle bottom 50. In addition, the clinician can also apply an upward force to an at least partially horizontal section of the needle or a connector to the needle. In the embodiment shown, this is the connector section 56 of needle 52. The extent to which the needle is pulled is limited by the connectors, which are formed so that at the extreme upper limit, the pointed end 58 remains within needle well 22. In this case, a bounce-back is confined within the needle well 22 and would not expose the clinician to pointed end 58. Once extracted, needle guard 10 can be locked to prevent accidental reactivation of the needle.

Figure 11:
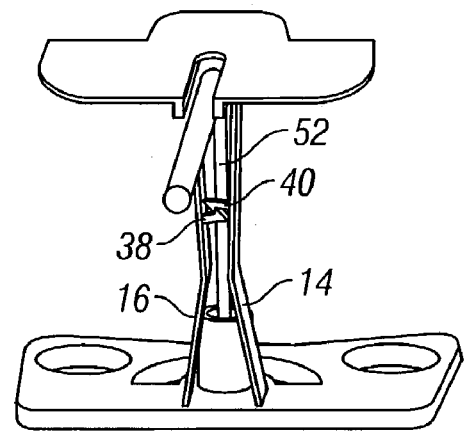
FIG. 11 is a perspective rear view of a needle guard assembly in its retracted state, where the needle is surrounded by the needle well, and the connectors in the locked position.

FIG. 11 provides a prospective view of the needle assembly after the needle has been retracted from the patient. Note that the locks parts 38 and 40, shown as latches, are locked, to secure connectors 14 and 16 in the upright position, so that pointed end 58 of needle 52 is secured withing either needle well 22 of base 12 or guide aperture 21 of guide 20 (FIG. 8). In another embodiment (not shown), a separate clip is used to lock the connectors in a secured position. Optionally, needle cover 62, whether integral with the needle guard 10 or as a separate piece, is reattached to cover well 22 as a further way of preventing the accidental exposure of pointed end 58 (not shown).

Figure 12:
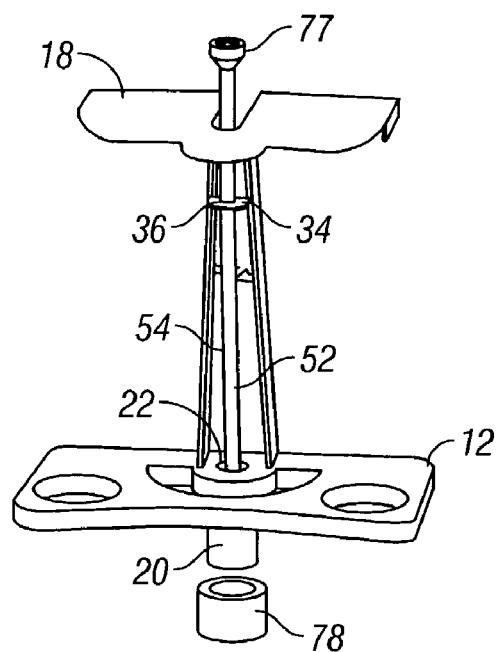
FIG. 12 illustrates an embodiment of a needle guard assembly using a straight needle.

In FIG. 12, an embodiment of the needle guard assembly is shown, in which the needle is a substantially straight needle, with an integral connector 77. In this case, guide 20 is attached to base bottom 26 of base 12, to allow the needle to approach the patient at an angle other than a substantially perpendicular angle. To provide an added measure of safety, cap 78 is used to cover needle well 22 at guide 20. In this embodiment, base 12 or a section thereof is optionally resilient so that guide 20 can be deformed into a non-perpendicular angle relative to the base. As demonstrated, various different needle types can be used with needle guards according to the invention. As a further example, a straight needle that is attached to a connector that forms an angle with the needle can also be used with the needle guard.

In a preferred embodiment, the needle guard is molded as an one-piece plastic part. However, different materials approved for medical devices may be used. In addition, different components of the needle guard may be made separately, then secured to one another. Although not shown, the guide may be merged into the base, such that the base provides a sufficiently long needle well to prevent the needle point from being accidentally exposed during retraction from the patient.

I claim:

1. A needle guard comprising:
   a base having a needle well;
   a handle attached to the base by a connector, and
   a needle holder capable of securing a medical needle having a pointed end,
   wherein the extent to which the base can be moved away from the handle is limited by the connector, and the walls of the needle well completely surrounds the needle point when the handle is distally extended away from the base, and
   wherein the connector is structured so that the handle is capable of being pushed towards the base such that the needle is guided beyond the needle well,
   said needle guard further comprising a cover attachable to said base capable of covering said needle well when the needle point is in the well.

2. A needle guard for a medical needle having a portion with a pointed end adapted for insertion into a patient, said needle guard comprising:
   a base having a needle well;
   a handle attached to the base,
   said base and handle being connected by a connector, and
   a needle holder capable of securing a medical needle having a pointed end,
   wherein movement of the base toward or away from said handle is limited by said connector, and
   said needle well completely surrounds and covers the needle point when the handle is distally extended away from said base and when said needle point is in said well, and
   wherein said connector is structured so that said handle is capable of being pushed towards said base to guide said point of said needle into said well and through said base,
   said connector comprising connected accordion walls which are locked together
   when in extended position and which fold toward one another when said handle is pushed towards said base to move said needle into said well,
   said needle at all times being covered by said needle guard except for the portion inserted in a patient.

3. The needle guard according to claim 2, said connector further comprising a lock that, when locked, is capable of preventing the base and the handle from being pushed towards each other.

4. The needle guard according to claim 2, further comprising a positioning gap on the base.

5. The needle guard according to claim 2, wherein the holder is capable of holding a medical needle comprising a piercing section connected to a connector section by an angular section, such that the pointed end of the needle is at an end of the piercing section distal from the connector section.

6. The needle guard according to claim 2, wherein the base further comprises a guide attached to a top portion of the base and the guide has a guide aperture therethrough in communication with and contributing to the needle well.

7. The needle guard according to claim 6, wherein the guide is attached to a bottom portion of the base and the guide has a guide aperture therethrough in communication with and contributing to the needle well.

8. The needle guard according to claim 2, wherein the holder is capable of holding a straight needle.

9. The needle assembly according to claim 2, wherein the base and the handle are attached by a connector selected from the group consisting of two accordion walls, two telescoping walls, a spring and a resiliently compressible material.

10. The needle assembly according to claim 2, wherein the needle has a piercing section, connected to a connector section by a angled section, and wherein the piercing section has the pointed end distal from the connector section, and the connector section is connected to a medical tube.

11. The needle assembly according to claim 2, wherein a portion of the base is sufficiently resilient to deform the guide to a non-perpendicular angle.

12. The needle guard according to claim 11, wherein said base has positioning gaps adapted to receive the finger tips of a user for locating a point of use.

13. The needle guard according to claim 11, wherein said base has a gap for receiving said needle point therein and said well has guide means for directing said needle through said well and base and into said gap.

14. A method of using a medical needle having a pointed end comprising:
  providing a needle guard having a base comprising a needle well, a handle attached to the base by a foldable connector, a locking means that, when locked, is capable of keeping the handle and the base at distal ends of the connector, a needle holder securing the needle to the guard,
  wherein the handle is initially extended away from the base, such that a pointed end of the needle is surrounded by the walls of the needle well;
  placing the needle guard substantially against a patient so that the needle well is above an area for the needle to be inserted;
  folding the connector against the base by pressing the handle towards the base thus inserting the needle into the patient;
  pulling the handle away from the base to unfold the connector and retract the needle from the patient, such that the connectors directs the pointed end back within the needle well;
  locking the locking means, and
  maintaining the needle fully covered at all time except for the portion inserted into the patient.

15. The method recited in claim 14, with the additional steps of locking the connector in extended unfolded condition prior to insertion of the needle into the patent, and unlocking the locking means when the needle is inserted in the patient.

16. A needle guard for a medical needle intended for use to prevent unintended needle sticks, said needle having a pointed end adapted for insertion into a patient at a time of use, said needle guard comprising:
  a base having a needle well;
  a handle attached to the base,
  said base and handle being connected by a connector, and
  a needle holder capable of securing a medical needle having a pointed end,
    wherein movement of the base toward or away from said handle is limited by said connector, and
    said needle well completely surrounds and covers the needle point when the handle is distally extended away from said base and when said needle point is in said well, and
  wherein said connector is structured so that said handle is capable of being pushed towards said base to guide said point of said needle into said well and through said base,
    said connector comprising connected walls which are locked together
  when in extended position and which move together when said handle is pushed towards said base to move said needle into said well,
    said needle at all times while in said guard, before, during and after insertion, being shielded from unintended needle sticks.

* * * * *